Figure 1:
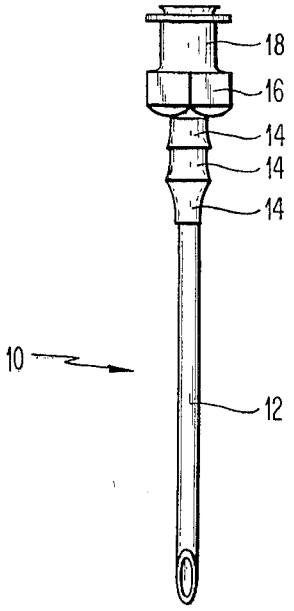
FIG. 1 PRIOR ART
Figure 2:
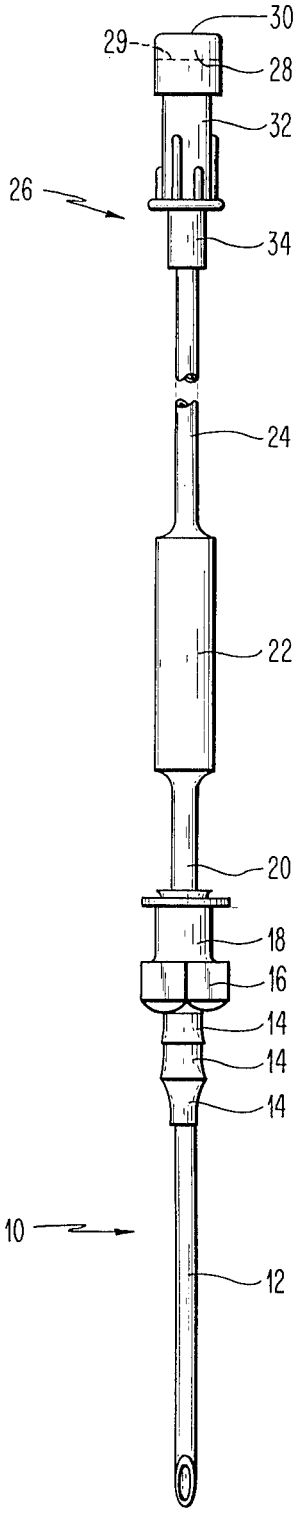

DEFENSIVE PUBLICATION

UNITED STATES PATENT AND TRADEMARK OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent and Trademark Office makes no assertion as to the novelty of the disclosed subject matter.

PUBLISHED JANUARY 6, 1976

942 O.G. 189

T942,001

INTRAVENOUS CATHETER ATTACHMENT DEVICE HAVING A REMOVABLE, RESEALABLE INJECTION ELEMENT

Winifred T. Tuttle, 61 Duracher Terrace, Poughkeepsie, N.Y. 12603

Continuation of abandoned application Ser. No. 342,198, Mar. 16, 1973. This application May 29, 1975, Ser. No. 581,814

**Int. Cl. A61m *5/00***

U.S. Cl. 128—214 R

1 Sheet Drawing. 9 Pages Specification

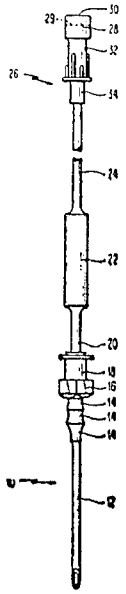

This is an intravenous catheter attachment device for connection to an intravenous catheter which is injected into the vein of a person. The intravenous catheter attachment device is cooperatively and quickly attached to an intravenous catheter in order to provide a complete unit to be left on the arm, leg or other portion of a person's body ready for instant injection of medication into the vein of the person. For example, people suffering from coronary thrombosis or emboli require intermittent injection of heparin which is a fast acting anti-coagulant. Thus, a vein of the person requiring the medication must be accessible at all times for the purpose of permitting the heparin to be injected therein when needed. The disclosed intravenous catheter attachment device utilizes an injection resealable latex rubber member 28 which is connected via, preferably, a plastic tube 24 to a plastic element 20 which in turn is removably engaged into the Luer-Lok end of, preferably, a Teflon catheter 12 which catheter is in the vein of the patient.

INTRAVENOUS CATHETER ATTACHMENT DEVICE HAVING A REMOVABLE, RESEALABLE INJECTION ELEMENT

Original Filed May 29, 1975